United States Patent [19]

Kubicki et al.

[11] Patent Number: 5,201,326
[45] Date of Patent: Apr. 13, 1993

[54] TAMPON FOR MEDICAL OR HYGIENIC PURPOSES AND METHOD OF MAKING THE SAME

[75] Inventors: Jörn Kubicki, Nürnberg; Norbert Rink, Wendelstein, both of Fed. Rep. of Germany

[73] Assignee: VP-Schickedanz, Nürnberg, Fed. Rep. of Germany

[21] Appl. No.: 574,421

[22] Filed: Aug. 28, 1990

[30] Foreign Application Priority Data

Aug. 30, 1989 [DE] Fed. Rep. of Germany ....... 3928677

[51] Int. Cl.⁵ .............................................. A61F 6/06
[52] U.S. Cl. .................... 128/832; 604/363; 424/431
[58] Field of Search ............... 128/832, 833; 604/361, 604/363; 424/431

[56] References Cited

U.S. PATENT DOCUMENTS

| | | | |
|---|---|---|---|
| 3,481,335 | 12/1969 | Beutlich | 604/11 |
| 3,776,001 | 12/1973 | Hanke | 424/431 |
| 3,999,549 | 12/1976 | Poncy et al. | |
| 4,211,769 | 7/1980 | Okada et al. | 514/15 |
| 4,274,410 | 6/1981 | Chvapil | |

FOREIGN PATENT DOCUMENTS

| | | | |
|---|---|---|---|
| 3122954 | 4/1983 | Fed. Rep. of Germany | |
| 3320218 | 12/1984 | Fed. Rep. of Germany | 604/361 |
| 0892386 | 3/1962 | United Kingdom | 128/832 |

*Primary Examiner*—Randall L. Green
*Assistant Examiner*—R. Clarke
*Attorney, Agent, or Firm*—Spencer, Frank & Schneider

[57] ABSTRACT

A rod-shaped medical tampon for releasing an active substance, including (a) a tampon core of compressed fibers selected from the group consisting of cellulose fibers, cotton fibers, and acetate fibers; (b) a tampon cover surrounding said tampon core and being firmly bonded to one another by a glue, the tampon cover comprising a hardened collagen foam or a hardened gelatin foam impregnated with a retardant including a dissolved active substance to be released; and (c) a retrieval string connected to at least one of said tampon core and said tampon cover.

10 Claims, 2 Drawing Sheets

TAMPON FOR MEDICAL OR HYGIENIC PURPOSES AND METHOD OF MAKING THE SAME

CROSS REFERENCE TO RELATED APPLICATION

This application claims the priority of Federal Republic of Germany Application No. P 39 28 677.0 filed Aug. 30, 1989, which is incorporated herein by reference.

BACKGROUND OF THE INVENTION

The present invention relates to a rod-shaped multi-layer tampon for medical or hygienic purposes and to a method for its manufacture.

Rod-shaped tampons for hygienic purposes, particularly for feminine hygiene purposes, are known. These tampons generally comprise a strand of wound cotton compacted by radial pressure. The strand of cotton usually comprises a mixture of cotton and cellulose to which swellable substances may have been added in order to increase its fluid absorption capacity. At one end, the rod-shaped product, which is rather rigid after the pressing process, has a retrieval string which serves to remove the tampon from the body cavity after use.

In addition to the mentioned hygienic tampons, other types of tampons are known which primarily serve medical purposes. They are also introduced into a body cavity but their principal purpose there is not to absorb bodily fluids, for example, menstrual fluids, but rather to discharge active substances which serve to treat the body cavity. Such a tampon is disclosed, for example, in Federal Republic of Germany Patent No. 3,122,954. This tampon is made of foamed polyvinyl alcohol acetal containing medications for use in various fields of therapeutic medicine.

One of the main problems in tampons intended to discharge active substances into the body cavity is that these active substances must be discharged slowly over as long as possible a period of time, without the reverse process of the absorption of fluids from the body cavity interfering with the release of these active substances. It has been found that this cannot be satisfactorily accomplished with tampons made of cellulose or other fibers or of open-pored plastic foams, such as foamed polyurethane, polyvinyl alcohol, cellulose or rubber, due to their absorptive action.

Annular sponges impregnated with contraceptive agents are known. These sponges are made of native collagen in the form of fibrous proteins which are introduced into the vaginal cavity as required. Sponge rings of this type are disclosed, for example, in U.S. Pat. No. 4,274,410. The material is soft-elastic so that it is not suitable for the production of tampons or medical tampons. However, it is well suited as a carrier for the mentioned active substances and has been found satisfactory in this respect.

SUMMARY OF THE INVENTION

It is an object of the present invention to provide a rod-shaped, self-supporting tampon for medical or hygienic purposes which can be introduced without the aid of an applicator, which stores active substances for a longer period of time, and which releases the active substances slowly at an approximately uniform rate without having the release interfered by the absorption of fluids into the tampon.

This object and others to become apparent as the specification progresses, are accomplished by the invention, according to which, briefly stated, the rod-shaped tampon has a tampon core of compressed fibers; a tampon cover comprising hardened collagen or gelatine foam impregnated with an active substance; and a retrieval string. The present invention also relates to methods for producing the tampon.

The multi-layer structure makes it possible for the tampon to be sufficiently rigid and self-supporting so that it can be introduced into the body cavity without a applicator. In addition, the feature of a core of compressed fibers offers the possibility of attaching a retrieval string so that the tampon can be reliably removed from the body cavity after a longer period of use. Such a retrieval string could not be anchored sufficiently firmly in a tampon composed solely of foamed gelatine. It has been found to be particularly advantageous to manufacture the tampon core of compressed cellulose or cellulose acetate fibers since these result in a sufficiently firm core.

The tampon cover should preferably have a density of 15 to 60 g/l and a porosity of at least 20 to 60 pores/cm. Active substances can be used which, due to their solubility and diffusion behavior, can be incorporated in the tampon cover without a carrier (retardant) substance. In one embodiment of the present invention, the active substance is not deposited in its pure form in the tampon cover but is included or dissolved in a retardant substance, for example, a suitable fatty substance, with which the tampon cover is then impregnated. Triglycerides and/or partial glycerides of higher fatty acids having a melting point between 34° C. and 37° C. are suitable retardant substances. Advantageously, the active substance in the tampon cover has a radially increasing or decreasing concentration gradient in order to produce the desired release behavior. Such an arrangement of the active substance in the cover can be realized by impregnating the cover after its manufacture in a radially inward or radially outward direction with the active substance or with a solution of the active substance in a retardant.

The type of the active substance depends on the type of treatment to be given; for example it may be composed of antibiotics, sulfonamides, antimycotics, fungicides or hormones.

Preferably, the tampon cover is composed of air-dried or freeze-dried foamed collagen or foamed gelatine which is hardened or additionally hardened with the aid of aldehydic hardening agents. The hardening agent may be incorporated in the foamed substance already during its manufacture. It is also possible to bring the hardening agent in contact with the foamed substance at a later time when the foamed substance has already been processed into a tampon cover. Gaseous or liquid aldehydes, such as, for example, formaldehyde, glutaraldehyde or similar substances are suitable hardening agents.

It is important for the tampon core and the tampon cover to be bonded sufficiently firmly with one another. During the manufacturing process it may be advantageous for both components to be glued together, for example with the aid of a gelatine or collagen adhesive layer applied to the tampon core.

The retrieval string preferably forms a loop which penetrates the tampon core and the tampon cover. In this way, the two parts are prevented from separating when the tampon is removed from the body cavity.

The tampon surface may have a lubricant coating, such as a solid fat which softens at about 34.5° C., that is at body temperature.

Tests indicate that it is advantageous for the diameter of the tampon core to be about one third of the total diameter of the tampon. However, a larger range from about one quarter to three quarters of the total diameter is also acceptable.

DESCRIPTION OF THE PREFERRED EMBODIMENTS

Figure 1:
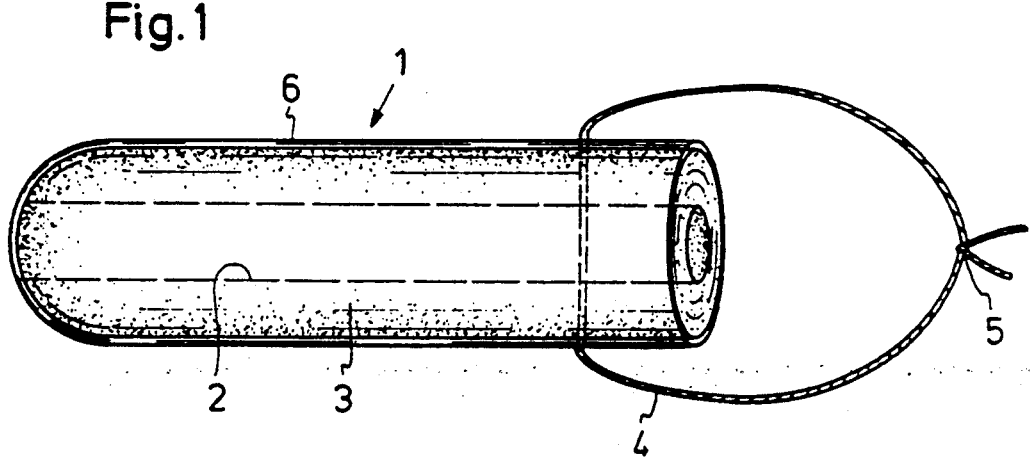
FIGS. 1, 2 and 3 are schematic side elevational views of three preferred embodiments of the invention.
Figure 2:
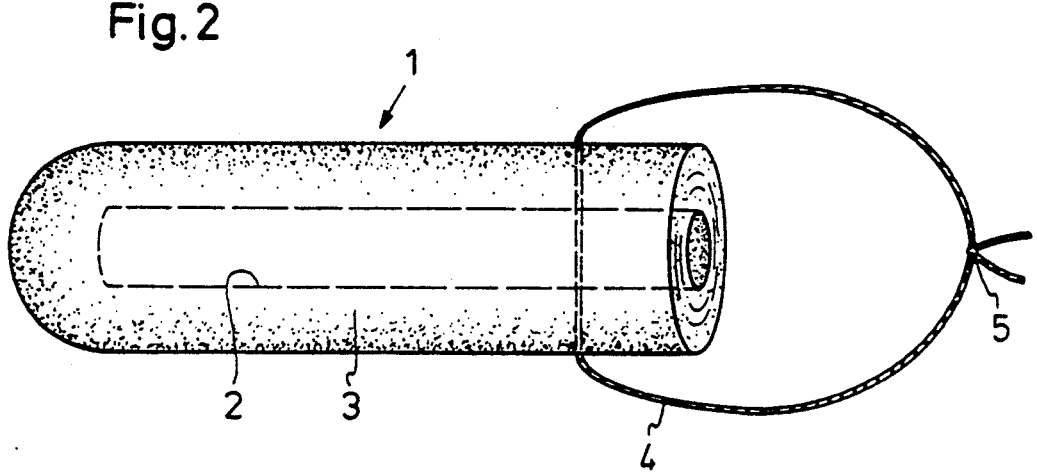
Figure 3:
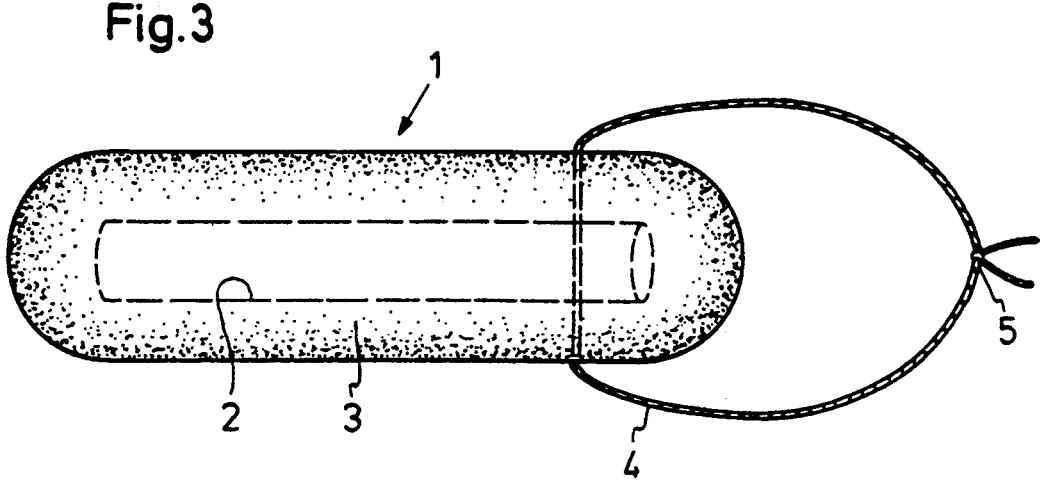

Turning now to FIGS. 1, 2 and 3, a tampon generally designated at 1 is composed of a tampon core 2 and a tampon cover 3. The tampon core 2 is composed of compressed fiber material, preferably compressed cellulose acetate fibers. The tampon cover 3 is composed of post-hardened collagen or gelatine foam which is impregnated with a fatty substance containing an active substance. In the embodiment of FIG. 1, the tampon 1 has a tampon core 2 that extends essentially along the entire tampon length. In the embodiment of FIG. 2, the tampon core 2 is introduced from the rear and takes up only about three quarters of the length of the tampon. In the embodiment according to FIG. 3, the tampon core 2 is disposed in the interior of the tampon and is enclosed on all sides by the foam material of the tampon cover 3.

The core 2 and the cover 3 are penetrated by a retrieval string 4 which forms a loop by tying a knot 5. The surface of the tampon cover is preferably coated with a lubricant film 6.

Figure 4:
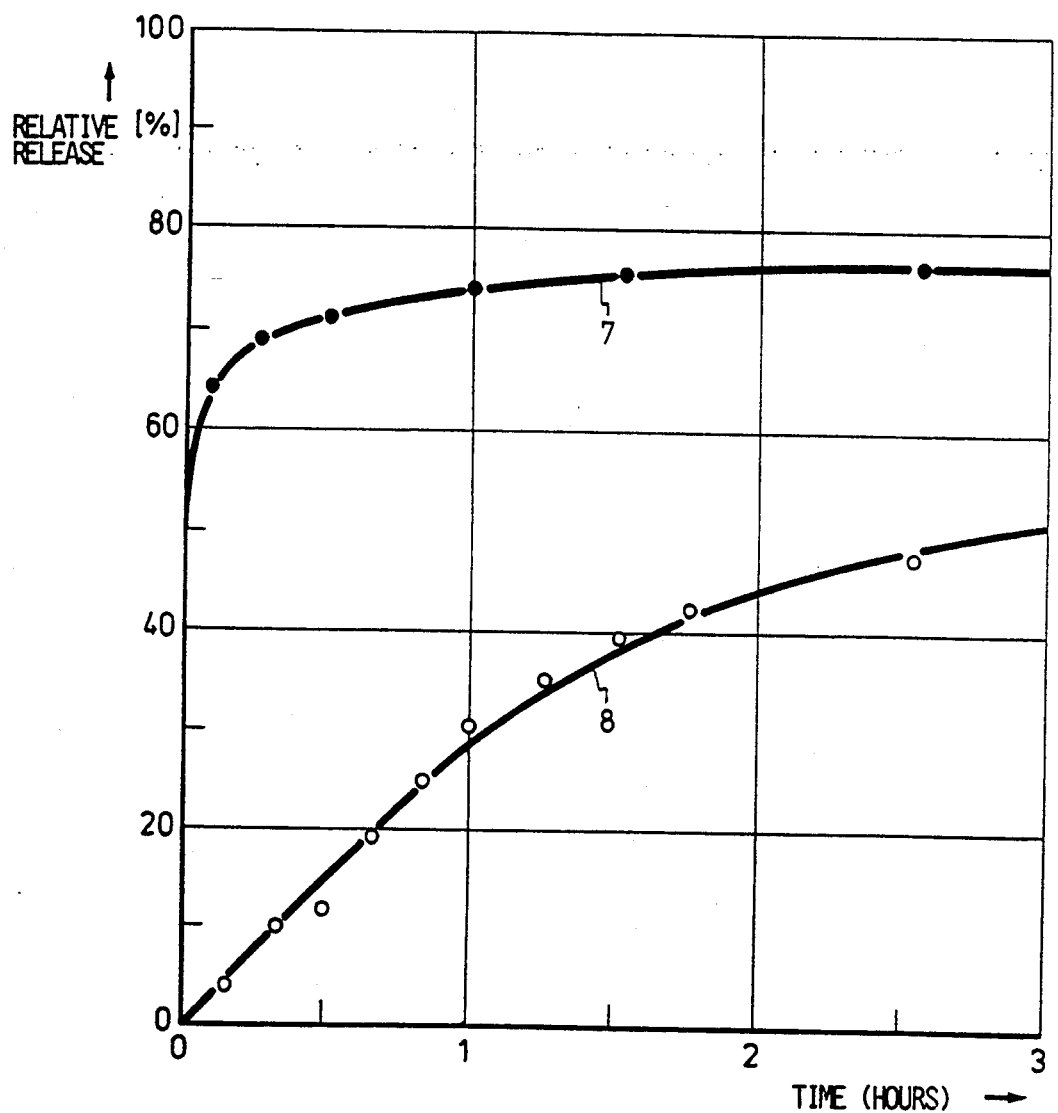
FIG. 4 is a graph comparing medication release rates for a product according to the invention to those for a prior art product.

The diagram of FIG. 4 shows a comparison of the relative release of a suppository substance from two differently constructed tampons in a laboratory apparatus for determining the active substance release. For this purpose, the tampon is disposed in a dialysis tube, whose exterior is exposed to a hydrostatic pressure of 35 cm column of water. Physiologic saline solution is conducted through the interior of the dialysis tube at a flow rate of 0.2 ml/10 minutes. The test temperature was 37° C. The curves show the release of the suppository substances from the two tampons in percent over time.

The upper curve 7 relates to a cellulose core having a diameter of 0.8 cm and a length of 5 cm, coated on its exterior with 4 g of the suppository substance. The core represents a non-retarding tampon.

The lower curve 8 shows the behavior of a gelatine tampon of the same size whose gelatine foam cover is impregnated with 4 g of the same suppository substance. It is seen that the rate of relative release increases much slower initially and is over the entire test period more uniform than in the tampon according to curve 7. The active substance dissolved in the suppository substance would be released and discharged into the interior of the body cavity in the same manner.

The multi-layer tampon according to the invention can be produced in various ways.

In a preferred process, initially the tampon core is given the shape of a cylindrical rod by the compression of fibers, for example cellulose fibers, cellulose acetate fibers or the like. In a further process step, a tampon cover of collagen or gelatine foam is produced. The cover is provided with a central longitudinal opening whose inner diameter corresponds to the outer diameter of the tampon core. The foamed substance has to be hardened depending on the composition and type of the collagen or gelatine substance. Such hardening is effected in a known manner by means of suitable aldehydes, for example formaldehyde, glutaraldehyde or the like. The hardening agent may be added to the foamed substance immediately or may be introduced into the foamed substance at a later point in time. In a further process step, the tampon core is encased in a collagen or gelatine adhesive layer and then the core is introduced into the longitudinal opening of the tampon cover. Thereafter, a retrieval string is pulled through the tampon core and the tampon cover, and the ends of the retrieval string are knotted together. Then the tampon is impregnated by saturation or spraying with the melted fat which contains the active substance and which has been heated to a temperature between 40° and 50° C. Thereafter, the tampon is permitted to cool to a temperature of less than 20° C. on its circumference. Then the tampon is coated with a molten lubricant at a temperature of about 40° C. in an immersion or spray process.

Another preferred manufacturing process comprises the following process steps:

Initially, a tampon core of compressed fibers is produced in the shape of a rod. Then a retrieval string is drawn through the tampon core and a loop is formed by knotting its ends together. The tampon core is then placed into the center of a mold which is filled by spraying in collagen or gelatine foam from an extruder either before or after the insertion of the string. In this process, core and foamed cover are firmly bonded together so that a separate encasing of the core with a gelatine adhesive layer is not required. After completion of the raw tampon, it is impregnated by saturation or spraying with a molten fat containing the active substance. Then, if necessary, the tampon may be coated with a lubricant in an immersion or spray process.

The following substances or mixtures of substances are suitable, among others, as impregnation or coating substance:

triglycerides or partial glycerides of fatty acids having 12 to 18 carbon atoms;
polyethylene glycol;
polyethylene sorbitan fatty acid ester;
cetyl phthalate;
propylene glycol monostearate and propylene glycol distearate;
branched fatty alcohols.

The mentioned substances may also be used in mixtures with one another.

It will be understood that the above description of the present invention is susceptible to various modifications, changes and adaptations, and the same are intended to be comprehended within the meaning and range of equivalents of the appended claims.

What is claimed is:

1. A rod-shaped medical tampon for releasing an active substance, comprising:

(a) a tampon core of compressed fibers selected from the group consisting of cellulose fibers, cotton fibers, and acetate fibers;

(b) a tampon cover surrounding said tampon core and being firmly bonded to one another by a glue, the tampon cover comprising a hardened collagen foam or a hardened gelatin foam impregnated with a retardant including a dissolved active substance to be released; and (c) a retrieval string connected to at least one of said tampon core and said tampon cover.

2. A tampon as defined in claim 1, further comprising an external lubricant coating.

3. A tampon as defined in claim 1, wherein said tampon cover has a density of about 15 to 60 g/l and a porosity of at least about 20 to 60 pores/cm.

4. A tampon as defined in claim 1, wherein said retardant comprises triglycerides of higher fatty acids having a melting point between about 34° C. and 37° C.

5. A tampon as defined in claim 1, wherein said retardant comprises partial glycerides of higher fatty acids having a melting point between about 34° C. and 37° C.

6. A tampon as defined in claim 4, wherein said retardant further comprises partial glycerides of higher fatty acids having a melting point between about 34° C. and 37° c.

7. A tampon as defined in claim 1, wherein said retrieval string forms a loop which penetrates said tampon core and said tampon cover.

8. A tampon as defined in claim 2, wherein said external lubricant coating comprises a hard fat that softens at about 30° C. to 35° C.

9. A tampon as defined in claim 8, wherein said hard fat softens at about 34.5° C.

10. A tampon as defined in claim 1, wherein the tampon is rod shaped and further wherein the diameter of said tampon core is about one third of the total diameter of said tampon.

* * * * *